US012167928B2

(12) United States Patent
Wang et al.

(10) Patent No.: US 12,167,928 B2
(45) Date of Patent: Dec. 17, 2024

(54) REMOTE OPERATION CONTROL SYSTEM, REMOTE OPERATION CONTROL METHOD, AND NON-TRANSITORY STORAGE MEDIUM

(71) Applicant: BOE TECHNOLOGY GROUP CO., LTD., Beijing (CN)

(72) Inventors: Yuan Wang, Beijing (CN); Ran Tao, Beijing (CN)

(73) Assignee: Beijing BOE Technology Development Co., Ltd., Beijing (CN)

( * ) Notice: Subject to any disclaimer, the term of this patent is extended or adjusted under 35 U.S.C. 154(b) by 355 days.

(21) Appl. No.: 17/635,856

(22) PCT Filed: Feb. 9, 2021

(86) PCT No.: PCT/CN2021/076380
§ 371 (c)(1),
(2) Date: Feb. 16, 2022

(87) PCT Pub. No.: WO2021/169815
PCT Pub. Date: Sep. 2, 2021

(65) Prior Publication Data
US 2022/0296200 A1 Sep. 22, 2022

(30) Foreign Application Priority Data
Feb. 25, 2020 (CN) ........................ 202010116258.3

(51) Int. Cl.
*A61B 6/00* (2024.01)
*A61B 6/46* (2024.01)

(52) U.S. Cl.
CPC ............ *A61B 6/548* (2013.01); *A61B 6/4441* (2013.01); *A61B 6/465* (2013.01); *A61B 6/547* (2013.01); *A61B 6/4405* (2013.01)

(58) Field of Classification Search
None
See application file for complete search history.

(56) References Cited

U.S. PATENT DOCUMENTS 5,549,439 A * 8/1996 Ploem ...................... B25J 19/06 378/204
9,259,202 B2 * 2/2016 Yoshida ................ A61B 6/503
(Continued)

FOREIGN PATENT DOCUMENTS

CN 102047199 A 5/2011
CN 103085072 A 5/2013
(Continued)

OTHER PUBLICATIONS

Translation of DE 102009004766 A1 (Year: 2010).*
(Continued)

*Primary Examiner* — Thomas R Artman
(74) *Attorney, Agent, or Firm* — IP & T GROUP LLP

(57) ABSTRACT

A remote operation control system includes a simulation device, a target device and a control device. The control device is coupled to the simulation device and the target device, and is configured to determine first position data and first attitude data of the simulation device when the simulation device moves to a set state, and control the target device to move to a same state as the set state based on the first position data and the first attitude data.

16 Claims, 8 Drawing Sheets

(56) References Cited

U.S. PATENT DOCUMENTS

| | | | | |
|---|---|---|---|---|
| 9,649,080 | B2 * | 5/2017 | Kwak | A61B 6/0487 |
| 9,795,357 | B2 * | 10/2017 | Carelsen | A61B 6/461 |
| 9,962,138 | B2 * | 5/2018 | Schweizer | A61B 6/467 |
| 10,076,295 | B2 * | 9/2018 | Gemmel | A61B 6/547 |
| 10,310,292 | B2 * | 6/2019 | Tian | F16M 13/04 |
| 10,517,553 | B2 * | 12/2019 | Barker | A61B 6/4441 |
| 10,573,023 | B2 * | 2/2020 | Crawford | A61B 6/461 |
| 10,922,897 | B2 * | 2/2021 | Maeda | A61B 6/466 |
| 11,109,825 | B2 * | 9/2021 | Barker | A61B 6/4458 |
| 11,696,814 | B2 * | 7/2023 | Nagao | A61B 90/361 600/102 |
| 11,759,269 | B2 * | 9/2023 | Zhou | A61B 1/00149 606/1 |
| 11,937,968 | B2 * | 3/2024 | Engel | A61B 6/08 |
| 2011/0029903 | A1 | 2/2011 | Schooleman et al. | |
| 2013/0266123 | A1 * | 10/2013 | Yoshida | A61B 6/504 378/165 |
| 2014/0314205 | A1 * | 10/2014 | Carelsen | A61B 6/547 378/62 |
| 2015/0223764 | A1 * | 8/2015 | Kwak | H01J 37/20 378/63 |
| 2015/0374325 | A1 * | 12/2015 | Shimizu | A61B 6/4441 378/98 |
| 2016/0235386 | A1 * | 8/2016 | Schweizer | A61B 6/547 |
| 2016/0296185 | A1 * | 10/2016 | Gemmel | A61B 6/547 |
| 2018/0120585 | A1 | 5/2018 | Tian et al. | |
| 2018/0279980 | A1 * | 10/2018 | Barker | A61B 6/4458 |
| 2019/0221046 | A1 * | 7/2019 | Maeda | A61B 6/5264 |
| 2019/0311490 | A1 * | 10/2019 | Crawford | A61B 6/461 |
| 2019/0328343 | A1 * | 10/2019 | Barker | A61B 6/4476 |
| 2019/0365499 | A1 | 12/2019 | Nagao et al. | |
| 2020/0054403 | A1 | 2/2020 | Zhou et al. | |
| 2022/0022839 | A1 * | 1/2022 | Engel | A61B 6/547 |
| 2022/0296200 | A1 * | 9/2022 | Wang | A61B 6/548 |

FOREIGN PATENT DOCUMENTS

| | | | | |
|---|---|---|---|---|
| CN | 106249761 | A | 12/2016 | |
| CN | 106354043 | A | 1/2017 | |
| CN | 108161904 | A | 6/2018 | |
| CN | 108268056 | A | 7/2018 | |
| CN | 108803673 | A | 11/2018 | |
| CN | 110238879 | A | 9/2019 | |
| CN | 110325093 | A | 10/2019 | |
| CN | 110464470 | A | 11/2019 | |
| CN | 111317490 | A | 6/2020 | |
| DE | 102009004766 | A1 * | 7/2010 | A61B 6/4441 |

OTHER PUBLICATIONS

Office Action for the Chinese Patent Application No. 202010116258.3 issued by the Chinese Patent Office on Mar. 10, 2023.

* cited by examiner

REMOTE OPERATION CONTROL SYSTEM, REMOTE OPERATION CONTROL METHOD, AND NON-TRANSITORY STORAGE MEDIUM

CROSS-REFERENCE TO RELATED APPLICATIONS

This application is a national phase entry under 35 USC 371 of International Patent Application No. PCT/CN2021/076380, filed on Feb. 9, 2021, which claims priority to Chinese Patent Application No. 202010116258.3, filed on Feb. 25, 2020, which are incorporated herein by reference in their entirety.

TECHNICAL FIELD

The present disclosure relates to the technical field of remote control of medical equipment, and in particular, to a remote operation control system, a remote operation control method, and a non-transitory storage medium.

BACKGROUND

In the field of medical equipment, C-arms (or U-arms, G-arms) are mainly used for fluoroscopy and spot film in various operations. Generally, there are two ways to adjust a C-arm (or U-arm, G-arm) in actual use. A first way is for a doctor to adjust it on site. In this way, the doctor needs to come in and out of an imaging room frequently, which not only wastes a lot of time, but also consumes the doctor's energy. A second way is for a doctor to control a C-arm through an interface. In this way, the doctor needs to constantly learn the latest operation method to proceed with the operation; moreover, the doctor cannot have an intuitive understanding of an actual position and attitude of the C-arm, and may need to try several times to achieve an expected effect.

In both of the above two ways, it is not possible to obtain a current position and attitude of a device or a component thereof in real time and intuitively, and it is difficult to adjust the device to an expected position and attitude, resulting in low work efficiency and poor accuracy.

SUMMARY

In one aspect, a remote operation control system is provided. The remote operation control system includes a simulation device, a target device and a control device. The control device is coupled to the simulation device and the target device. The control device is configured to determine first position data and first attitude data of the simulation device when the simulation device moves to a set state, and control the target device to move to a same state as the set state based on the first position data and the first attitude data.

In some embodiments, the simulation device includes at least one driving component and at least one first sensor. The at least one driving component is coupled to the control device, and the at least one driving component is configured to drive the simulation device to move to the set state under control of the control device. The at least one first sensor is connected to the at least one driving component in one-to-one correspondence, and each first sensor is configured to obtain a movement amount of a driving component of a corresponding driving component connected to the first sensor when the simulation device moves from a previous state to the set state. The control device is coupled to the at least one first sensor, and the control device is configured to determine the first position data and the first attitude data based on position data and attitude data of the simulation device when the simulation device is in the previous state, and a movement amount of the at least one driving component.

In some embodiments, the control device is further configured to: obtain a current state of the target device; generate a control instruction including a movement control amount based on second position data and second attitude data of the target device in the current state, and the first position data and the first attitude data, and send the control instruction to the target device. The control instruction is used for controlling the target device to move to the same state as the set state.

In some embodiments, the movement control amount includes at least one linear displacement control amount and/or at least one rotation angle control amount.

In some embodiments, the control device is further configured to: control the simulation device to move to the set state in response to a first operation of an operator instructing the simulation device to move; and/or, determine whether the simulation device has moved to the set state in response to a second operation of the operator instructing the simulation device to move to the set state.

In some embodiments, the remote operation control system further includes at least one second sensor. The at least one second sensor is configured to detect the second position data and/or the second attitude data of the target device in the current state. The control device is coupled to the at least one second sensor, and the control device is further configured to obtain the second position data and/or the second attitude data detected by the at least one second sensor.

In some embodiments, the remote operation control system further includes an interaction device. The interaction device is configured to obtain information of the current state of the target device, and display the information of the current state of the target device. The information of the current state of the target device includes the second position data and the second attitude data of the target device; and/or, an image of the target device.

In some embodiments, the interaction device is coupled to the control device, and the interaction device is configured to obtain the second position data and the second attitude data of the target device in the current state from the control device, and display the second position data and the second attitude data of the target device. And/or, the remote operation control system further includes a photographing device coupled to the interaction device. The photographing device is configured to photograph the image of the target device, and send the image of the target device to the interaction device, so that the interaction device displays the image of the target device.

In some embodiments, the control device is further configured to obtain a current state of the target device, and control the simulation device to move to the same state as the target device based on second position data and second attitude data of the target device in the current state, under a predetermined condition.

In some embodiments, the predetermined condition includes at least one of following: fine-tuning a pose of the target device; or resetting the target device to an initial state.

In some embodiments, the target device is a C-arm, and the simulation device is a simulated C-arm.

In some embodiments, the simulated C-arm includes an L-shaped part, a C-shaped part, and an X-axis rotary motion mechanism. The L-shaped part includes an X-axis linear motion mechanism, a Y-axis linear motion mechanism, and a Y-axis rotary motion mechanism connecting the X-axis linear motion mechanism and the Y-axis linear motion mechanism. The X-axis rotary motion mechanism connects the X-axis linear motion mechanism and the C-shaped part. The Y-axis rotary motion mechanism is configured to make the X-axis linear motion mechanism rotate around a Y axis relative to the Y-axis linear motion mechanism; and the X-axis rotary motion mechanism is configured to make the C-shaped part rotate around an X axis relative to the X-axis linear motion mechanism.

In some embodiments, the Y-axis linear motion mechanism includes a first motor and a first encoder. The first motor is configured to drive the X-axis linear motion mechanism to move linearly based on a first movement control amount, and the first encoder is configured to detect a rotation amount of an output shaft of the first motor, so as to determine a linear movement amount of the X-axis linear motion mechanism. The X-axis linear motion mechanism includes a second motor and a second encoder. The second motor is configured to drive the C-shaped part to move linearly based on a second movement control amount, and the second encoder is configured to detect a rotation amount of an output shaft of the second motor, so as to determine a linear movement amount of the C-shaped part. The Y-axis rotary motion mechanism includes a third motor and a third encoder. The third motor is configured to drive the X-axis linear motion mechanism to rotate relative to the Y-axis linear motion mechanism based on a third movement control amount, and the third encoder is configured to detect a rotation amount of an output shaft of the third motor, so as to determine a rotation amount of the X-axis linear motion mechanism. The X-axis rotary motion mechanism includes a fourth motor and a fourth encoder. The fourth motor is configured to drive the C-shaped part to rotate relative to the X-axis linear motion mechanism based on a fourth movement control amount, and the fourth encoder is configured to detect a rotation amount of an output shaft of the fourth motor, so as to determine a rotation amount of the C-shaped part. The C-shaped part includes a fixed structure, an arc-shaped structure, a fifth motor, and a fifth encoder. A guide rail is provided on the fixed structure, and the arc-shaped structure is slidably connected to the guide rail. The fifth motor is configured to drive the arc-shaped structure to rotate relative to the fixed structure based on a fifth movement control amount, and the fifth encoder is configured to detect a rotation amount of an output shaft of the fifth motor, so as to determine a rotation amount of the arc-shaped structure.

In another aspect, a remote operation control method is provided. The remote operation control method includes: determining first position data and first attitude data of a simulation device when the simulation device moves to a set state; and controlling a target device to move to a same state as the set state based on the first position data and the first attitude data.

In some embodiments, determining the first position data and the first attitude data of the simulation device when the simulation device moves to the set state includes: obtaining a movement amount of at least one driving component of the simulation device when the simulation device moves from a previous state to the set state; and determining the first position data and the first attitude data based on position data and attitude data of the simulation device when the simulation device is in the previous state, and the movement amount of the at least one driving component.

In some embodiments, controlling the target device to move to the same state as the set state based on the first position data and the first attitude data includes: obtaining a current state of the target device; generating a control instruction including a movement control amount based on second position data and second attitude data of the target device in the current state, and the first position data and the first attitude data, and sending the control instruction to the target device. The control instruction is used for controlling the target device to move to the same state as the set state.

In some embodiments, the movement control amount includes at least one linear displacement control amount and/or at least one rotation angle control amount.

In some embodiments, the remote operation control method further includes: controlling the simulation device to move to the set state in response to a first operation of an operator instructing the simulation device to move; and/or, determining whether the simulation device has moved to the set state in response to a second operation of the operator instructing the simulation device to move to the set state.

In some embodiments, the remote operation control method further includes: obtaining a current state of the target device; and controlling the simulation device to move to the same state as the target device based on second position data and second attitude data of the target device in the current state, under a predetermined condition.

In some embodiments, the predetermined condition includes at least one of following: fine-tuning a pose of the target device; or resetting the target device to an initial state.

In yet another aspect, a non-transitory computer-readable storage medium is provided. The non-transitory computer-readable storage medium has stored computer program instruction(s) that, when run on a computer, cause the computer to execute the remote operation control method as described in any of the above embodiments.

BRIEF DESCRIPTION OF THE DRAWINGS

In order to describe technical solutions in the present disclosure more clearly, accompanying drawings to be used in some embodiments of the present disclosure will be introduced briefly below. Obviously, the accompanying drawings to be described below are merely accompanying drawings of some embodiments of the present disclosure, and a person of ordinary skill in the art may obtain other drawings according to these drawings. In addition, the accompanying drawings to be described below may be regarded as schematic diagrams, and are not limitations on actual dimensions of products, actual processes of methods and actual timings of signals involved in the embodiments of the present disclosure.

DETAILED DESCRIPTION

Figure 1:
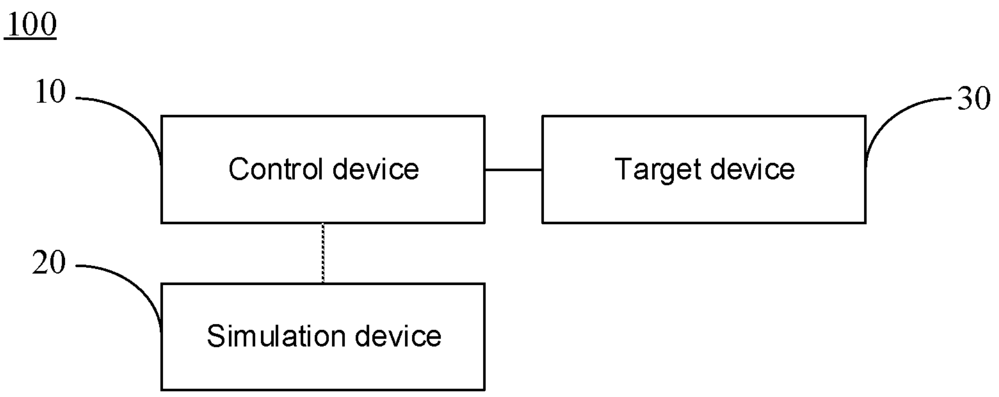
FIG. 1 is a structural diagram of a remote operation control system, in accordance with some embodiments.

Technical solutions in some embodiments of the present disclosure will be described clearly and completely below with reference to the accompanying drawings. Obviously, the described embodiments are merely some but not all embodiments of the present disclosure. All other embodiments obtained based on the embodiments of the present disclosure by a person of ordinary skill in the art shall be included in the protection scope of the present disclosure.

Unless the context requires otherwise, throughout the description and the claims, the term "comprise" and other forms thereof such as the third-person singular form "comprises" and the present participle form "comprising" are construed as an open and inclusive meaning, i.e., "including, but not limited to". In the description of the specification, the terms such as "one embodiment", "some embodiments", "exemplary embodiments", "example", "specific example" or "some examples" are intended to indicate that specific features, structures, materials or characteristics related to the embodiment(s) or example(s) are included in at least one embodiment or example of the present disclosure. Schematic representations of the above terms do not necessarily refer to the same embodiment(s) or example(s). In addition, the specific features, structures, materials, or characteristics may be included in any one or more embodiments or examples in any suitable manner.

Hereinafter, the terms "first" and "second" are used for descriptive purposes only, and are not to be construed as indicating or implying the relative importance or implicitly indicating the number of indicated technical features. Thus, a feature defined with "first" or "second" may explicitly or implicitly include one or more of the features. In the description of the embodiments of the present disclosure, the term "a plurality of/the to plurality of" means two or more unless otherwise specified.

In the description of some embodiments, the terms such as "coupled" and "connected" and derivatives thereof may be used. For example, the term "connected" may be used in the description of some embodiments to indicate that two or more components are in direct physical or electrical contact with each other. For another example, the term "coupled" may be used in the description of some embodiments to indicate that two or more components are in direct physical or electrical contact. However, the term "coupled" or "communicatively coupled" may also mean that two or more components are not in direct contact with each other, but still cooperate or interact with each other. The embodiments disclosed herein are not necessarily limited to the content herein.

The phrase "A and/or B" includes the following three combinations: only A, only B, and a combination of A and B.

The phrase "applicable to" or "configured to" used herein has an open and inclusive meaning, which does not exclude devices that are applicable to or configured to perform additional tasks or steps.

In addition, the use of the phrase "based on" indicates openness and inclusiveness, since a process, step, calculation or other action that is "based on" one or more of the stated conditions or values may be based on additional conditions or values exceeding those stated in practice.

Exemplary embodiments are described herein with reference to sectional views and/or plan views as idealized exemplary drawings. In the accompanying drawings, thickness of layers and sizes of regions are enlarged for clarity. Thus, variations in shape relative to the drawings due to, for example, manufacturing technologies and/or tolerances may be envisaged. The exemplary embodiments should not be construed as being limited to the shapes of the regions shown herein, but including shape deviations due to, for example, manufacturing. For example, an etched region shown to have a rectangular shape generally has a feature of being curved. Therefore, the regions shown in the accompanying drawings are schematic in nature, and their shapes are not intended to show actual shapes of the region in a device, and are not intended to limit the scope of the exemplary embodiments.

In order to keep the following description of the present disclosure clear and concise, detailed descriptions of known functions and known components may be omitted in the present disclosure.

For ease of understanding the present disclosure, a remote operation control system provided in some embodiments of the present disclosure is introduced in detail first.

FIG. 1 is a structural diagram of a remote operation control system 100 provided in some embodiments of the present disclosure. As shown in FIG. 1, the remote operation control system 100 includes a control device 10, a simulation device 20 and a target device 30. The control device 10 is coupled to the simulation device 20 and the target device 30.

The control device 10 is configured to determine first position data and first attitude data of the simulation device 20 when the simulation device 20 moves to a set state, and control the target device 30 to move to a same state as the set state based on the first position data and the first attitude data.

The simulation device 20 and the target device 30 may have a same structure. That is, the simulation device 20 may be a model constructed based on a production drawing of the target device 30. A size ratio, a color rendered on each component and an angle between the components of the simulation device 20 may all be the same as those of the target device 30. For example, in a case where the target device 30 is a C-arm, the simulation device 20 is a simulated C-arm; in a case where the target device 30 is a U-arm, the simulation device 20 is a simulated U-arm; and so forth. In some examples, a size of the simulation device 20 is the same as a size of the target device 30. In some other examples, the size of the simulation device 20 is different from the size of the target device 30. For example, the size of the simulation device 20 is smaller than the size of the target device 30.

In the remote operation control system 100 provided in some embodiments of the present disclosure, after the simulation device 20 moves to the set state, the control device 10 analyzes and calculates the first position data and the first attitude data of the simulation device 20 that is in the set state (that is, the control device 10 determines the first position data and the first attitude data of the simulation device 20), and controls the target device 30 to move to the same state as the set state based on the first position data and the first attitude data, thereby achieving remote operation control of the target device 30. In this way, the user does not need to adjust the target device 30 on site repeatedly, which saves the time for the user to adjust the target device 30 and improves the work efficiency.

In some embodiments, the result that the simulation device 20 moves to the set state may be achieved in a way that the control device 10 controls the simulation device 20 to move to the set state. In this case, the control device 10 may be configured to control the simulation device 20 to move to the set state in response to a first operation of an operator instructing the simulation device 20 to move.

Here, "the first operation of the operator instructing the simulation device 20 to move" may be an operation that the user inputs movement parameter(s) to the control device 10 and/or the user presets the movement parameter(s) in the control device 10. For example, the user may preset the movement parameter(s) based on a working mode or a principle of the remote operation control system 100, so that the control device 10 controls the simulation device 20 to move based on the preset movement parameter(s).

In actual work, there may be some unexpected situations that cause a set state of the simulation device 20 to be abnormal at the present moment. In this case, the user may input the movement parameter(s) through a terminal (such as a touch screen, physical buttons, etc.) in the remote operation control system 100, or other terminals (such as a mobile phone, a remote control, etc.) connected to the remote operation control system 100, so that the control device 10 controls the simulation device 20 to move after receiving the movement parameter(s) set by the user.

With this arrangement, it may be possible to achieve high precision control of the simulation device 20, and make it easier for the simulation device 20 to move to the set state directly. In addition, compared with a solution in which the control device 10 directly controls the target device 30 to move, in the embodiments of the present disclosure, by using the control device 10 to control the simulation device 20 to move to the set state first, and then controlling the target device 30 to move based on the state of the simulation device 20, it may be possible to avoid directly adjusting the target device 30 for many times, and thus reduce the loss of the target device 30 and the waste of resources.

The set state is a state that the user expects the target device 30 to move to. Therefore, before the control device 10 controls the target device 30 to move to the same state as the set state based on the first position data and the first attitude data of the simulation device 20, the user may check whether the simulation device 20 has moved to an expected state (i.e., the set state) first. If the user determines that the simulation device 20 has moved to the expected state, the control device 10 may control the target device 30 to move to the same state as the set state based on the first position data and the first attitude data of the simulation device 20 after a preset period of time or after receiving a confirmation instruction from the user. If the user determines that the simulation device 20 has not moved to the expected state, the user may send an intervention instruction to the control device 10, so that the control device 10 does not control the target device 30 to move until the user determines that the simulation device 20 has moved to the set state (at which time the control device 10 will control the target device 30 to move to the same state as the set state based on the first position data and the first attitude data corresponding to the set state).

Of course, after the user determines that the simulation device 20 has not moved to the expected state, the user may not send the intervention instruction to the control device 10. For example, every time after the simulation device 20 moves, the control device 10 controls the target device 30 to move once based on intermediate position data and intermediate attitude data obtained from each movement of the simulation device 20, until the simulation device 20 moves to the set state, so that the target device 30 moves to the same state as the set state.

Based on this, the control device 10 may be further configured to determine whether the simulation device 20 has moved to the set state in response to a second operation of the operator instructing the simulation device 20 to move to the set state. In this case, before the target device 30 is controlled to move to the same state as the set state based on the first position data and the first attitude data, it is determined whether the simulation device 20 has moved to the set state. In this way, it may be possible to further improve the accuracy of the state to which the target device 30 will move, and improve the accuracy in which the control device 10 controls the target device 30. As a result, excessive loss of the target device 30 caused by too many adjustments to the target device 30 may be avoided, and waste of resources may be avoided to a certain extent.

In some other embodiments, the result that the simulation device 20 moves to the set state may be achieved in a way that the user manually controls the simulation device 20 to move to the set state. In this case, since the user manually adjusts the simulation device 20 to the set state, the user does not need to learn about operation interfaces, learn the latest operation methods, or understand a relationship between data input through the operation interface and an actual state of the target device 30. The user may intuitively control the simulation device 20, so as to control the target device 30 to move to the same state as the set state. In this way, the operation difficulty of the user in using the remote operation control system 100 may be reduced, and the practicability of the remote operation control system 100 may be improved.

In some examples, the control device 10 is configured to determine whether the simulation device 20 has moved to the set state in response to the second operation of the operator instructing the simulation device 20 to move to the set state. In this way, the control device 10 may also determine whether the simulation device 20 has moved to the set state in a case where the user manually controls the simulation device 20. As a result, it is convenient for the control device 10 to control the target device 30 to move to the same state as the set state.

Figure 2:
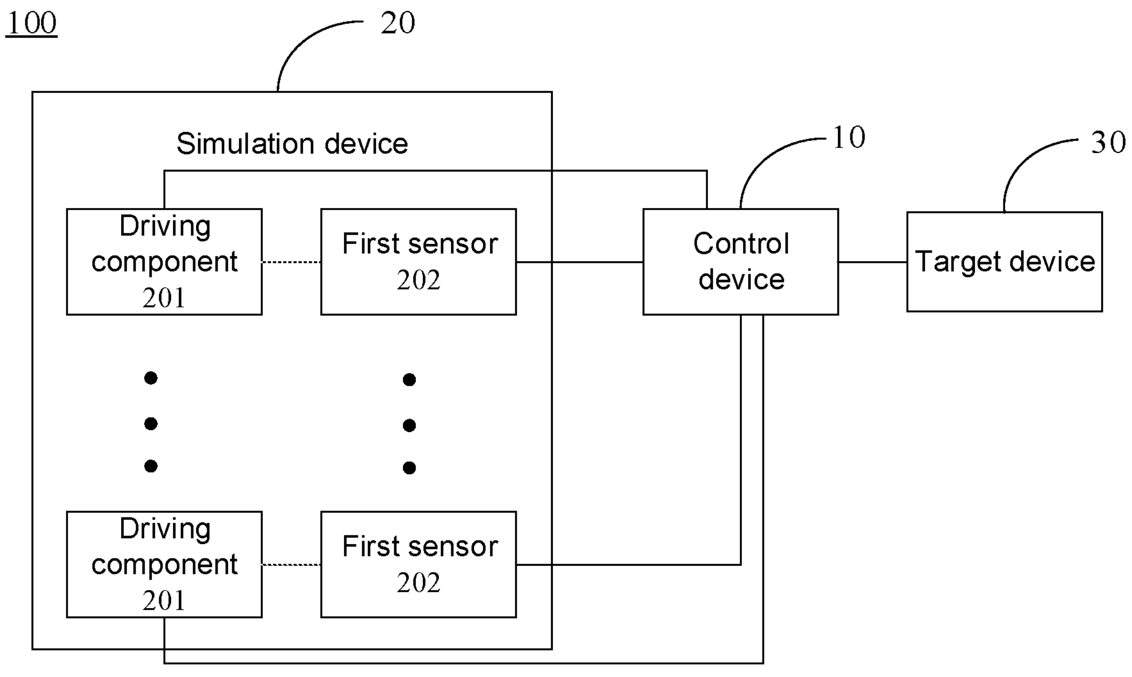
FIG. 2 is a structural diagram of another remote operation control system, in accordance with some embodiments.

In some embodiments, as shown in FIG. 2, the simulation device 20 includes at least one driving component 201 and at least one first sensor 202. The at least one driving component 201 is coupled to the control device 10, and the at least one driving component 201 is configured to drive the simulation device 20 to move to the set state under control of the control device 10. The at least one first sensor 202 is connected to the at least one driving component 201 in one-to-one correspondence. Each first sensor 202 is configured to obtain a movement amount of a corresponding driving component 201 connected to the first sensor 202 when the simulation device 20 moves from a previous state to the set state.

The control device 10 is coupled to the at least one first sensor 202. The control device 10 is configured to determine the first position data and the first attitude data based on position data and attitude data of the simulation device 20 when the simulation device 20 is in the previous state, and the movement amount of the at least one driving component 201.

For example, the driving component 201 may be a motor, and the first sensor 202 may be an encoder (e.g., a photoelectric encoder).

With this arrangement, the control device 10 may control the driving component(s) 201 to drive the simulation device 20 to move to the set state, and may also receive the movement amount of the driving component 201 through the first sensor 202 connected to the driving component 201 in one-to-one correspondence, so as to determine the first position data and the first attitude data.

It is worth noting that, in a case where the simulation device 20 is controlled by the control device 10 to move to the set state, by providing the at least one first sensor 202 in the simulation device 20, it may also help improve the accuracy in which the control device 10 controls the simulation device 20. For example, after the control device 10 transmits a control instruction to the simulation device 20, the at least one first sensor 202 may detect the actual movement amount of the at least one driving component 201 in the simulation device 20. By comparing the actual movement amount of the at least one driving component 201 and a movement control amount in the control instruction, the control device 10 may adjust the simulation device 20 again in a case where the actual movement amount of the driving component 201 is different from the movement control amount in the control instruction, until the actual movement amount of the driving component 201 is the same as the movement control amount in the control instruction, so as to ensure that the simulation device 20 moves to the set state.

In a case where the simulation device 20 is manually adjusted to the set state by the user, the control device 10 may obtain the movement amount of the driving component 201 connected to the first sensor 202 through the first sensor 202 when the simulation device 20 moves from the previous state to the set state, so as to determine the first position data and the first attitude data based on the position data and the attitude data of the simulation device 20 when the simulation device 20 is in the previous state, and the movement amount of the driving component 201. In this way, the control device 10 may drive the target device 30 to move to the same state as the set state in the case where the simulation device 20 is manually adjusted to the set state by the user.

Generally, a current state (including position and attitude) of the simulation device 20 is consistent with a current state (including position and attitude) of the target device 30. In this case, after the simulation device 20 moves to the set state, the control device 10 may control the target device 30 to move to the same state as the set state based on the first position data and the first attitude data of the simulation device 20. However, there are also cases where the current state of the simulation device 20 is not consistent with the current state of the target device 30 due to abnormalities or operation errors.

Therefore, in some embodiments, the control device 10 may further be configured to obtain the current state of the target device 30, generate a control instruction including a movement control amount based on second position data and second attitude data of the target device 30 in the current state, the first position data and the first attitude data, and send the control instruction to the target device 30. The control instruction is used for controlling the target device 30 to move to the same state as the set state.

With this arrangement, when the current state of the target device 30 is different from the current state of the simulation device 20, the control device 10 may control the target device 30 to move to the same state as the simulation device 20, which improves the stability of the remote operation control system 100.

In addition, it is worth noting that the target device 30 and the simulation device 20 are located in different environments. The target device 30 is located in an actual application scene (e.g., an image room). However, the target device 30 generally does not exist alone in the actual application scene. That is, there may be other devices around the target device 30. Therefore, in some embodiments of the present disclosure, the control device 10 is configured to detect the current state of the target device 30, and may further be configured to detect distances between the target device 30 and other devices. In this way, during a process in which the control device 10 controls the target device 30, it may also effectively prevent the target device 30 from colliding with other devices in the actual application scene, and thus effectively improve the security of the remote operation control system 100.

In some embodiments, the movement control amount may include at least one linear displacement control amount and/or at least one rotation angle control amount. For example, the movement control amount may include a linear displacement control amount and/or a rotation angle control amount of the target device 30 as a whole, and a linear displacement control amount and/or a rotation angle control amount of each component in the target device 30.

Figure 3:
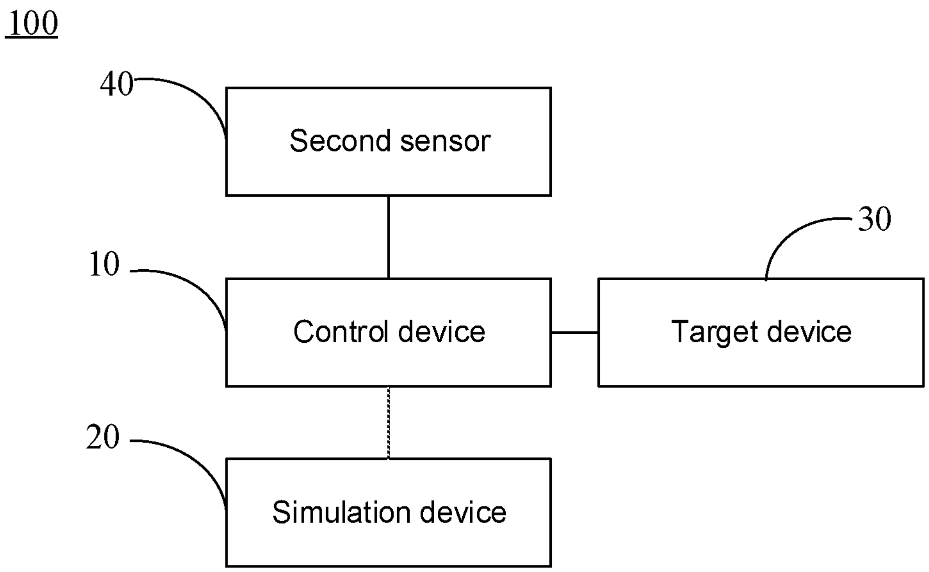
FIG. 3 is a structural diagram of yet another remote operation control system, in accordance with some embodiments.

In some embodiments, as shown in FIG. 3, the remote operation control system 100 further includes at least one second sensor 40. The second sensor(s) 40 are configured to detect the second position data and/or the second attitude data of the target device 30 in the current state. The control device 10 is coupled to the at least one second sensor 40, and the control device 10 is further configured to obtain the second position data and/or the second attitude data detected by the at least one second sensor 40.

For example, the second sensor 40 may be a gyroscope, a pressure sensor, etc. The second sensor 40 may be disposed on the target device 30, or not.

In the embodiments of the present disclosure, the remote operation control system 100 utilizes the control device 10 and the simulation device 20 to achive remote and real-time control of the target device 30, which improves work efficiency and reduces waste of resources and loss of target device 30 to a certain extent.

Figure 4:
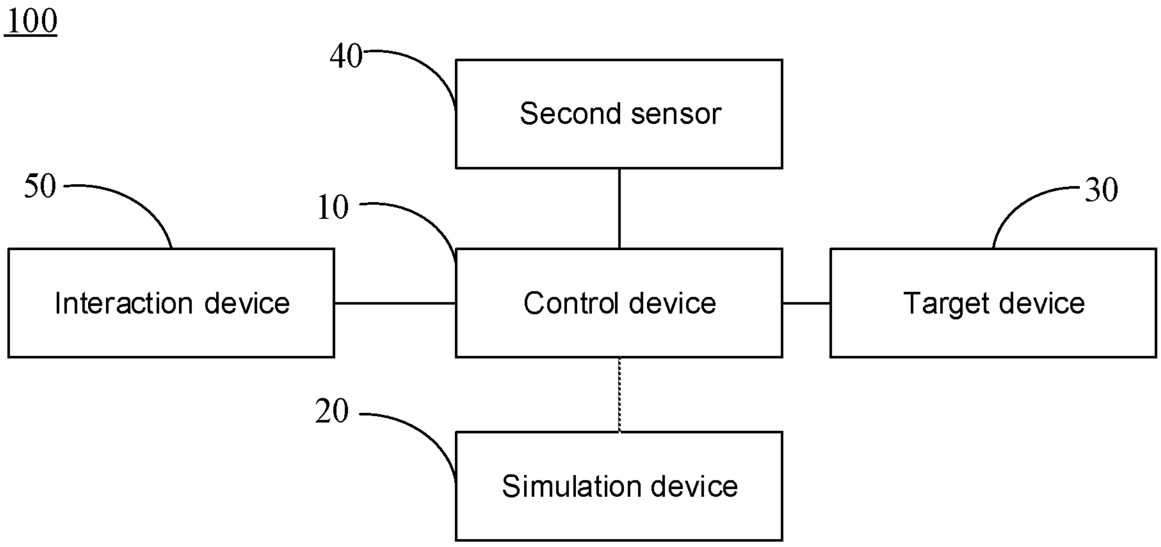
FIG. 4 is a structural diagram of still another remote operation control system, in accordance with some embodiments.
Figure 5:
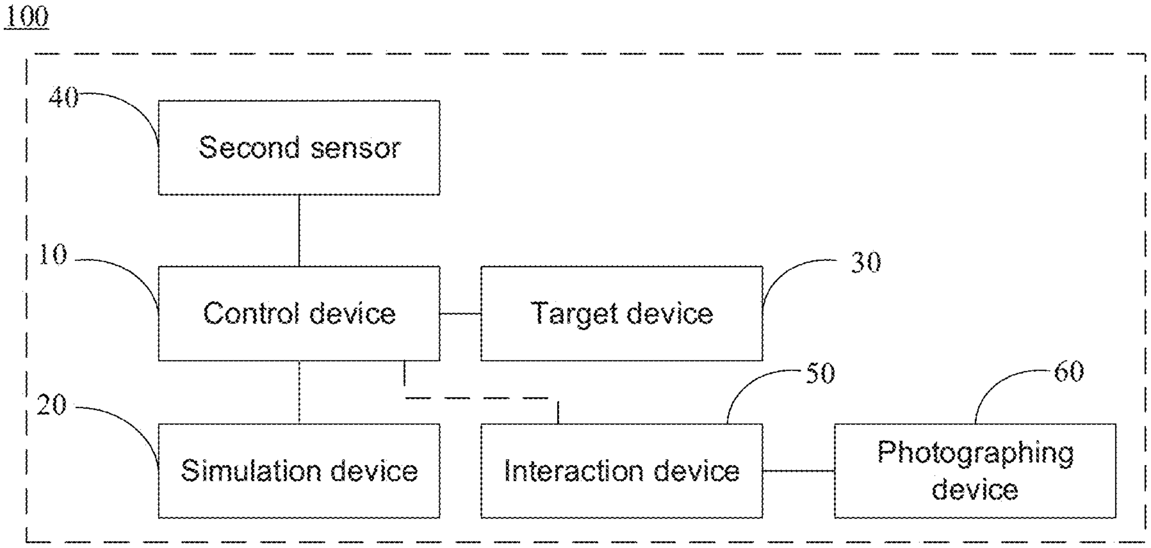
FIG. 5 is a structural diagram of still another remote operation control system, in accordance with some embodiments.

As shown in FIG. 4 or FIG. 5, in some embodiments, the remote operation control system 100 further includes an interaction device 50. The interaction device 50 is configured to obtain information of the current state of the target device 30, and display the information of the current state of the target device 30. The information of the current state of the target device 30 includes the second position data and the second attitude data of the target device 30. Or, the current state includes an image of the target device 30. Or, the current state includes the second position data, the second attitude data, and the image of the target device 30.

In a case where the information of the current state of the target device 30 includes the image of the target device 30, the interaction device 50 may display the current state of the target device 30 in two-dimensional six principle views, or in a draggable three-dimensional vision. In this way, it is convenient for the user to get a clear and intuitive understanding of the current state of the target device 30 through the interaction device 50.

In a case where the information of the current state of the target device 30 includes the second position data and the second attitude data of the target device 30, the interaction device 50 may display the second position data and the second attitude data of the target device 30. Furthermore, based on the second position data and the second attitude data of the target device 30, and initial position data and initial attitude data of the target device 30, the interaction device 50 may further calculate change values in the second position data and the second attitude data of the target device 30 relative to the initial position data and the initial attitude data thereof and display the change values.

In a case where the information of the current state of the target device 30 includes the image, the second position data and the second attitude data of the target device 30, the interaction device 50 may display the second position data, the second attitude data, and the image of the target device 30 at a same time. By combining image and data, it allows the user to get a more intuitive understanding of the current state of the target device 30, thus preventing the user from reaching a wrong conclusion about the current state of the target device 30 due to insensitivity to the connection between the data and the actual state.

In some embodiments, as shown in FIG. 4, the interaction device 50 is coupled to the control device 10, and the interaction device 50 is configured to obtain the second position data and the second attitude data of the target device 30 in the current state from the control device 10, and display the second position data and the second attitude data of the target device 30.

In some other embodiments, as shown in FIG. 5, the remote operation control system 100 further includes a photographing device 60 coupled to the interaction device 50. The photographing device 60 is configured to photograph the image of the target device 30, and send the image of the target device 30 to the interaction device 50, so that the interaction device 50 displays the image of the target device 30.

Every time after the remote operation control system 100 is used to adjust the target device 30 or before the remote operation control system 100 is used to adjust the target device 30, there's a need to fine-tune a pose of the target device 30 or even reset the target device 30 to an initial state. When fine-tuning the pose of the target device 30 or resetting the target device 30 to the initial state, the user needs to observe the current state of the target device 30 to determine whether the fine-tuned state of the target device 30 is the state expected by the user, or to determine whether the target device 30 is reset to the initial state.

Based on this, in some embodiments, the control device 10 is further configured to obtain the current state of the target device 30, and control the simulation device 20 to move to the same state as the target device 30 based on the second position data and the second attitude data of the target device 30 in the current state, under a predetermined condition.

With this arrangement, it may be ensured that the current state of the simulation device 20 is consistent with the current state of the target device 30 under the predetermined condition, and the user may know about the current state of the target device 30 by directly observing the current state of the simulation device 20 without entering the actual application screen where the target device 30 is located. Therefore, the user may save the time for entering the actual application screen where the target device 30 is located and thus improve work efficiency.

In some examples, the predetermined condition may include fine-tuning the pose of the target device 30. Or, the predetermined condition may include resetting the target device 30 to the initial state. Or, the predetermined condition may include fine-tuning the pose of the target device 30 and resetting the target device 30 to the initial state.

In some embodiments, the target device 30 is a C-arm, and the simulation device 20 is a simulated C-arm. For example, the target device 30 is a C-arm used in hospitals.

Figure 6:
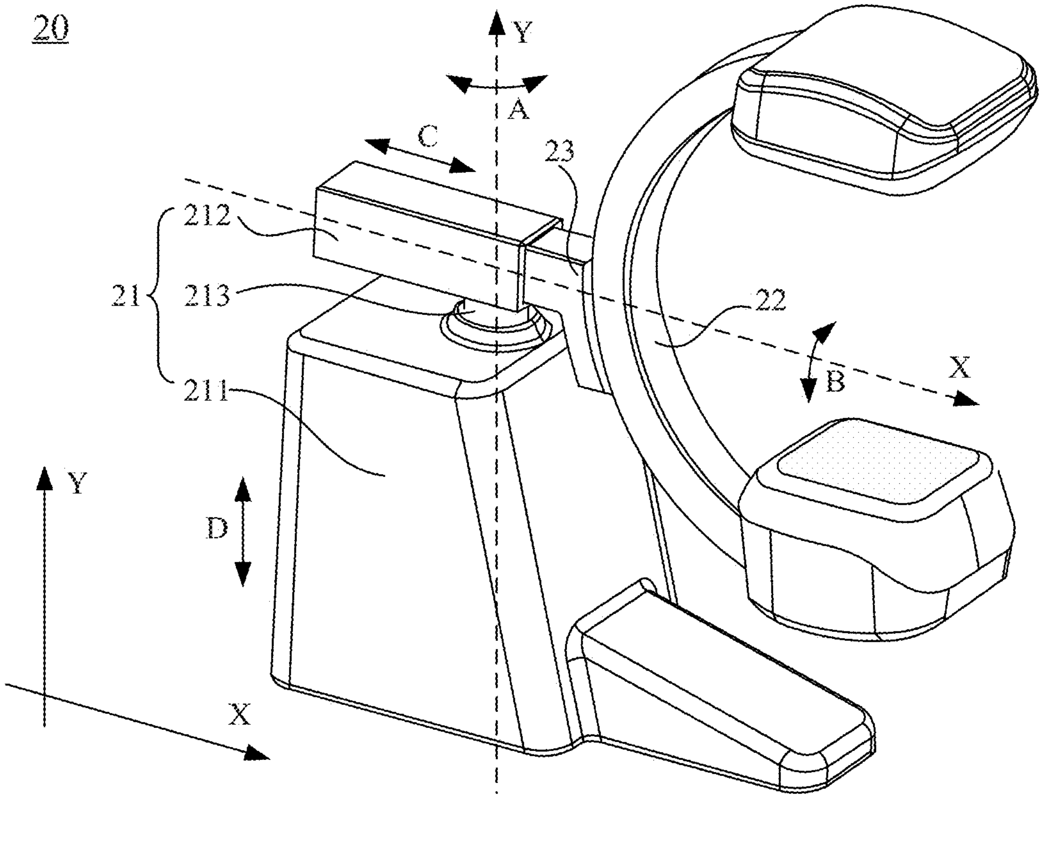
FIG. 6 is a structural diagram of a simulated C-arm, in accordance with some embodiments.
Figure 7:
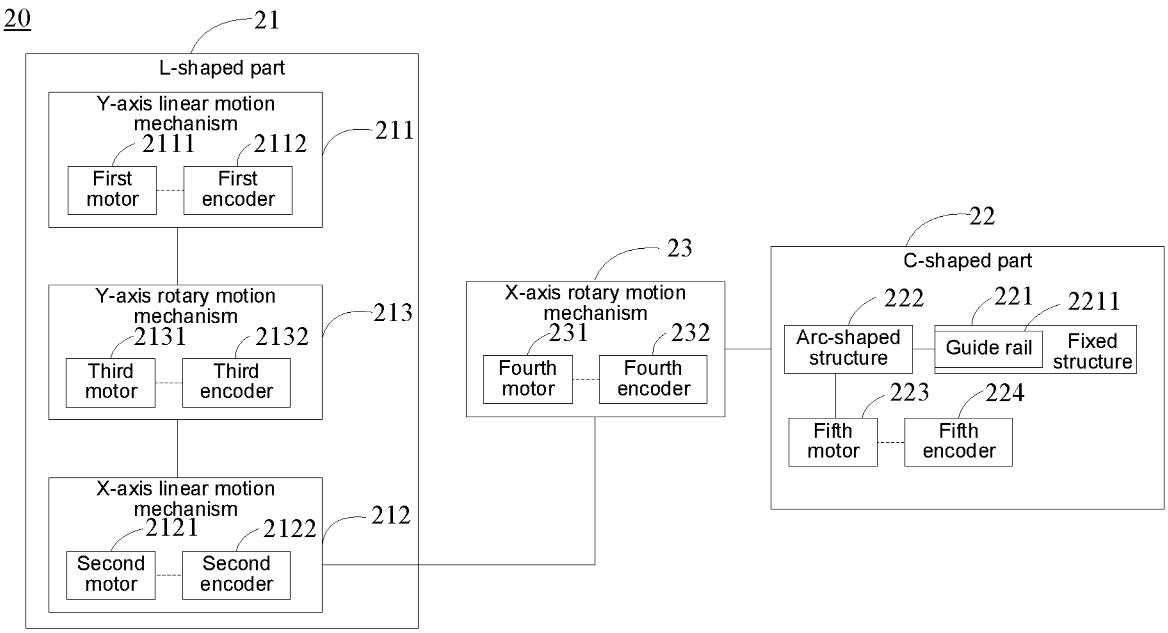
FIG. 7 is a structural diagram of another simulated C-arm, in accordance with some embodiments.

In some embodiments, as shown in FIGS. 6 and 7, the simulated C-arm (i.e., the simulation device 20) includes an L-shaped part 21, a C-shaped part 22 and an X-axis rotary motion mechanism 23. The L-shaped part 21 includes a Y-axis linear motion mechanism 211, an X-axis linear motion mechanism 212, and a Y-axis rotary motion mechanism 213 connecting the Y-axis linear motion mechanism 211 and the X-axis linear motion mechanism 212. The X-axis rotary motion mechanism 23 connects the X-axis linear motion mechanism 212 and the C-shaped part 22. The Y-axis rotary motion mechanism 213 is configured to make the X-axis linear motion mechanism 212 rotate around a Y axis relative to the Y-axis linear motion mechanism 211, and the rotation direction of the Y-axis rotary motion mechanism 213 is shown by the arrow A in FIG. 6. The X-axis rotary motion mechanism 23 is configured to make the C-shaped part 22 rotate around an X axis relative to the X-axis linear motion mechanism 212, and the rotation direction of the X-axis rotary motion mechanism 23 is shown by the arrow B in FIG. 6. The X axis and Y axis are perpendicular to each other.

In some embodiments, as shown in FIG. 7, the Y-axis linear motion mechanism 211 includes a first motor 2111 and a first encoder 2112. The first motor 2111 is configured to drive the X-axis linear motion mechanism 212 to move linearly based on a first movement control amount, and the movement direction of the X-axis linear motion mechanism 212 is shown by the arrow C in FIG. 6. The first encoder 2112 is configured to detect a rotation amount of an output shaft of the first motor 2111, so as to determine a linear movement amount of the X-axis linear motion mechanism 212.

In some embodiments, as shown in FIG. 7, the X-axis linear motion mechanism 212 may include a second motor 2121 and a second encoder 2122. The second motor 2121 is configured to drive the C-shaped part 22 to move linearly based on a second movement control amount, and the movement direction of the C-shaped part 22 is shown by the arrow D in FIG. 6. The second encoder 2122 is configured to detect a rotation amount of an output shaft of the second motor 2121, so as to determine a linear movement amount of the C-shaped part 22.

In some embodiments, as shown in FIG. 7, the Y-axis rotary motion mechanism 213 may include a third motor 2131 and a third encoder 2132. The third motor 2131 is configured to drive the X-axis linear motion mechanism 212 to rotate relative to the Y-axis linear motion mechanism 211 based on a third movement control amount. The third encoder 2132 is configured to detect a rotation amount of an output shaft of the third motor 2131, so as to determine a rotation amount of the X-axis linear motion mechanism 212.

In some embodiments, as shown in FIG. 7, the X-axis rotary motion mechanism 23 includes a fourth motor 231 and a fourth encoder 232. The fourth motor 231 is configured to drive the C-shaped part 22 to rotate relative to the X-axis linear motion mechanism 212 based on a fourth movement control amount. The fourth encoder 232 is configured to detect a rotation amount of an output shaft of the fourth motor 231, so as to determine a rotation amount of the C-shaped part 22.

In some embodiments, as shown in FIG. 7, the C-shaped part 22 includes a fixed structure 221, an arc-shaped structure 222, a fifth motor 223 and a fifth encoder 224. A guide rail 2211 is provided on the fixed structure 221. The arc-shaped structure 222 is slidably connected to the guide rail. The fifth motor 223 is configured to drive the arc-shaped structure 222 to rotate relative to the fixed structure 221 based on a fifth movement control amount. The fifth encoder 224 is configured to detect a rotation amount of an output shaft of the fifth motor 223, so as to determine a rotation amount of the arc-shaped structure 222.

For example, a toothed structure is provided on a side of the arc-shaped structure 222 proximate to the guide rail. The C-shaped part 22 may further include a gear, and the gear is engaged with the toothed structure on the arc-shaped structure 222. The fifth motor 223 is connected to the gear. The fifth motor 223 is further configured to drive the gear to rotate, so as to drive the arc-shaped structure 222 to rotate relative to the guide rail.

In some examples, the C-shaped part 22 may further include detection devices disposed on two ends of the arc-shaped structure 222. The detection devices include, for example, a charge coupled device (CCD) camera and an image intensifier.

In some examples, the first encoder 2112, the second encoder 2122, the third encoder 2132, the fourth encoder 232, and the fifth encoder 224 may be photoelectric encoders.

In this way, the remote operation control system 100 provided in some embodiments of the present disclosure may not only control the target device 30 remotely and in real time, but may also display the position and attitude of the target device 30 through the simulation device 20 in real time. As a result, the user does not need to enter the actual scene where the target device 30 is located repeatedly, which saves time and improves the work efficiency and accuracy.

Some embodiments of the present disclosure further provide a remote operation control method, and the remote operation control method may be performed on the remote operation control system 100. Since a working principle of the remote operation control method provided in the embodiments of the present disclosure is similar to a working principle of the remote operation control system 100 provided in the embodiments of the present disclosure, with regard to the implementation of the remote operation control method, reference may be made to the implementation of the system, and details will not be repeated here.

Figure 8:
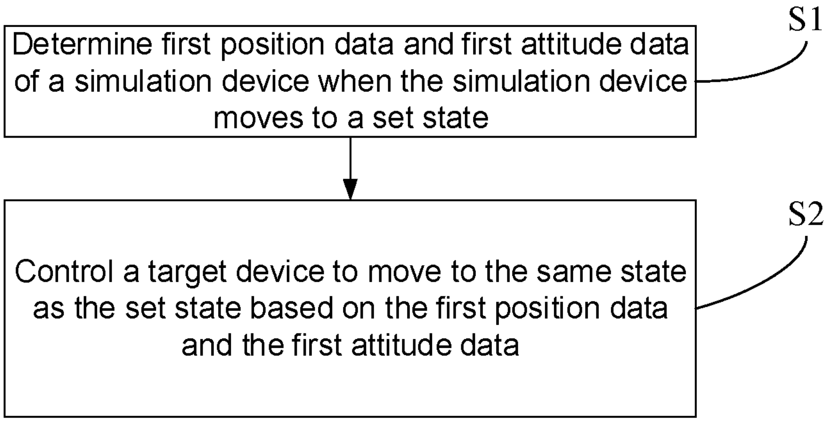
FIG. 8 is a flowchart of a remote operation control method, in accordance with some embodiments.

As shown in FIG. 8, the remote operation control method includes steps 1 and 2 (S1 and S2).

In S1, the first position data and the first attitude data of the simulation device 20 are determined when the simulation device 20 moves to the set state.

In S2, the target device 30 is controlled to move to the same state as the set state based on the first position data and the first attitude data.

With the remote operation control method provided in some embodiments of the present disclosure, the user does not need to adjust the target device 30 on site repeately. With the simulation device 20 and the control device 10, it may be possible to remotely control the target device 30 to move to the same state as the set state, which saves the time for the users to adjust the target device 30 and improves the work efficiency.

Figure 9:
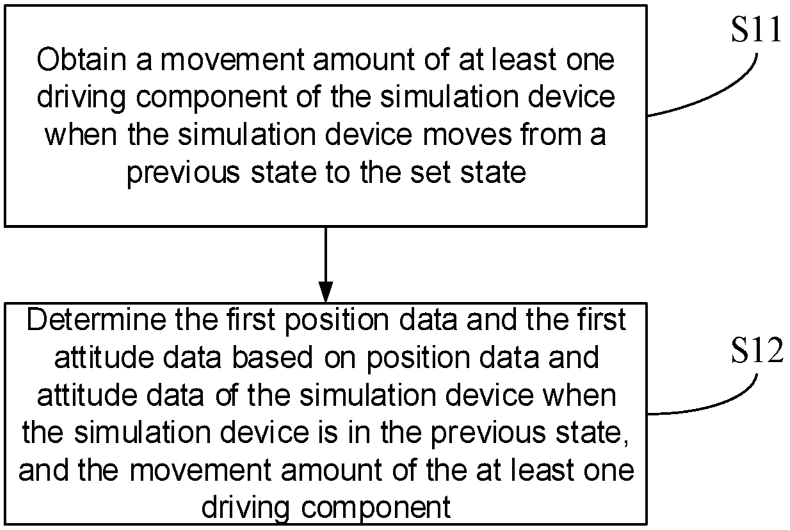
FIG. 9 is a flowchart of another remote operation control method, in accordance with some embodiments.

In some embodiments, the simulation device 20 further includes at least one driving component 201 (referring to FIG. 2). In this case, as shown in FIG. 9, 51 includes steps 11 and 12 (S11 and S12).

In S11, a movement amount of the at least one driving component 201 in the simulation device 20 is obtained when the simulation device 20 moves from a previous state to the set state.

In S12, the first position data and the first attitude data are determined based on position data and attitude data of the simulation device 20 when the simulation device 20 is in the previous state, and the movement amount of the at least one driving component 201.

Generally, a current state of the simulation device 20 is the same as a current state of the target device 30. Therefore, the control device 10 may directly control the target device 30 to move to the same state as the set state based on the first position data and the first attitude data determined after the simulation device 20 moves to the set state. However, there are also cases where the current state of the simulation device 20 is not consistent with the current state of the target device 30 due to abnormalities or operation errors.

Figure 10:
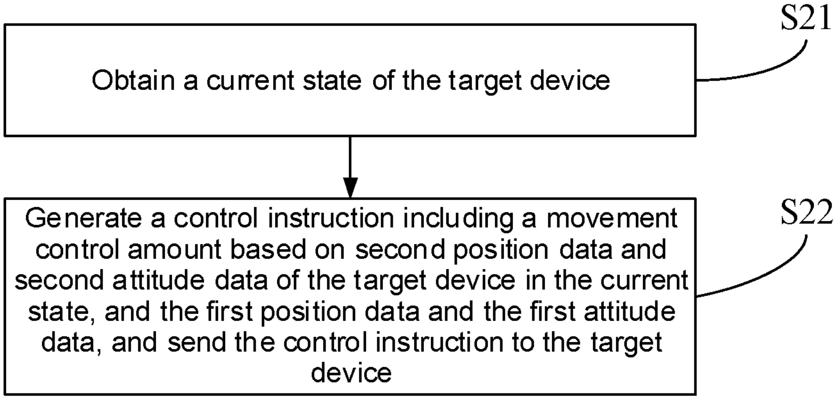
FIG. 10 is a flowchart of yet another remote operation control method, in accordance with some embodiments.

Based on this, in some embodiments, as shown in FIG. 10, S2 include steps 21 and 22 (S21 and S22).

In S21, the current state of the target device 30 is obtained.

In S22, a control instruction including a movement control amount is generated based on second position data and second attitude data of the target device 30 in the current state, and the first position data and the first attitude data, and the control instruction is sent to the target device 30. The control instruction is used for controlling the target device 30 to move to the same state as the set state.

The movement control amount includes, for example, at least one linear displacement control amount and/or at least one rotation angle control amount.

With this arrangement, when the current state of the target device 30 is different from the current state of the simulation device 20, the control device 10 may still control the target device 30 to move to the same state as the simulation device 20.

Figure 11A:
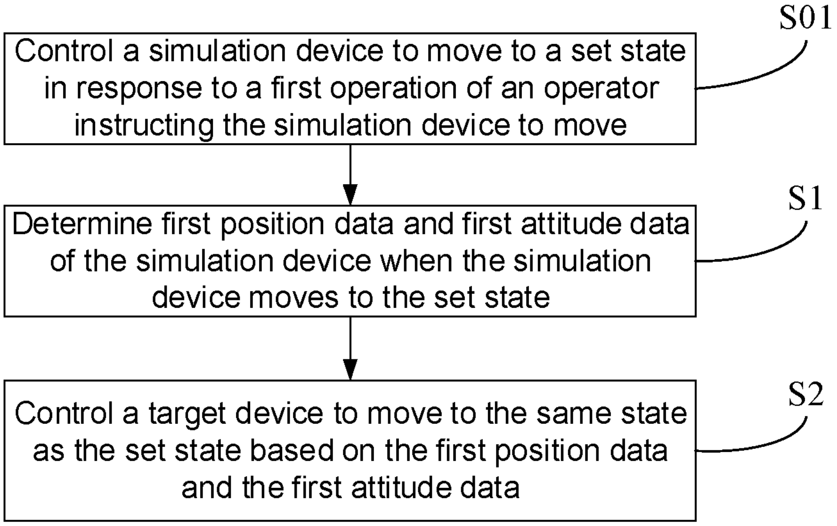
FIG. 11A is a flowchart of still another remote operation control method, in accordance with some embodiments.

In some embodiments, as shown in FIG. 11A, before S1, the remote operation control method further includes step 01 (S01).

In S01, the simulation device 20 is controlled to move to the set state in response to a first operation of an operator instructing the simulation device 20 to move.

In this way, the control device 10 directly controls the simulation device 20 to move, which realizes high precision control of the simulation device 20 and make it easier for the simulation device 20 to move to the set state directly.

Figure 11B:
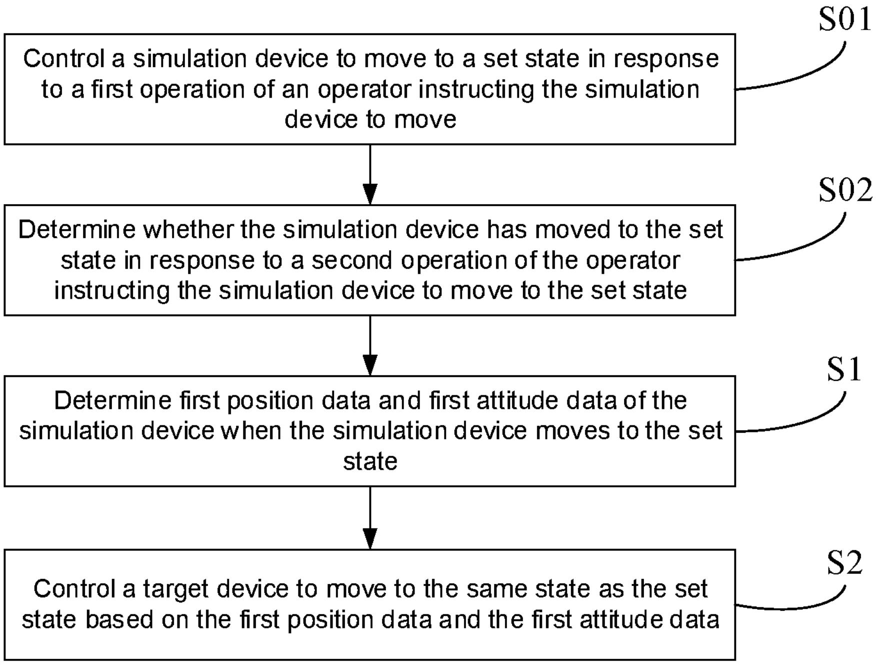
FIG. 11B is a flowchart of still another remote operation control method, in accordance with some embodiments.

In some other embodiments, as shown in FIG. 11B, before S1, the remote operation control method further include steps 01 and 02 (S01 and S02).

In S01, the simulation device 20 is controlled to move to the set state in response to a first operation of an operator instructing the simulation device 20 to move.

In S02, it is determined whether the simulation device 20 has moved to the set state in response to a second operation of the operator instructing the simulation device 20 to move to the set state.

In this way, before determining the first position data and the first attitude data, by determining whether the simulation device 20 has moved to the set state, it may be possible to further ensure the reliability of the first position data and the first attitude data, so that the target device 30 may move to the same state as the set state after the control device 10 controls the target device 30 to move.

Figure 11C:
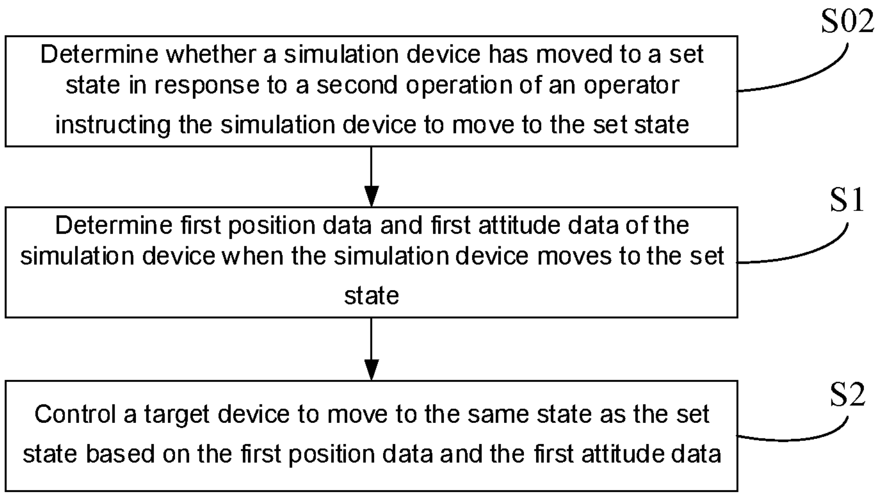
FIG. 11C is a flowchart of still another remote operation control method, in accordance with some embodiments.

Since the simulation device 20 may be manually controlled by the operator to move to the set state, in some other embodiments, as shown in FIG. 11C, the remote operation control method may only include S02 but not S01 before S1.

In this way, the control device 10 may determine whether the simulation device 20 has moved to the set state when the operator manually controls the simulation device 20 to move, which makes it easier for the control device 10 to control the target device 30 to move to the same state as the set state.

Figure 12:
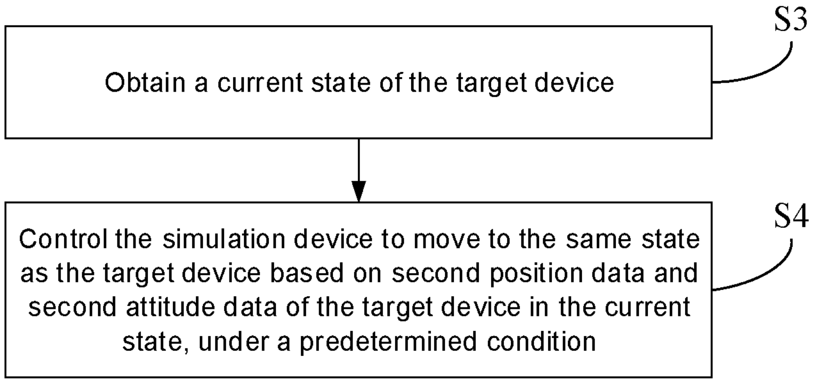
FIG. 12 is a flowchart of still another remote operation control method, in accordance with some embodiments.

In some embodiments, the remote operation control system 100 may also use the control device 10 to control the simulation device 20 to move to the same state as the target device 30. Based on this, as shown in FIG. 12, the remote operation control method further includes steps 3 and 4 (S3 and S4).

In S3, the current state of the target device 30 is obtained.

In S4, the simulation device 20 is controlled to move to the same state as the target device 30 based on the second position data and the second attitude data of the target device 30 in the current state, under a predetermined condition.

For example, the predetermined condition may include fine-tuning a pose of the target device 30. Or, the predetermined condition may include resetting the target device 30 to an initial state. Or, the predetermined condition may include both fine-tuning the pose of the target device 30 and resetting the target device 30 to the initial state.

In the embodiments of the present disclosure, by performing the above steps of the remote operation control method on the remote operation control system 100, it may be possible to realize remote and real-time control of the target device 30, and display the position and attitude of the target device 30 through the simulation device 20 in real time. As a result, the user does not need to enter the actual scene where the target device 30 is located repeatedly, which improves the work efficiency, and reduces the waste of resources and the loss of the target device 30 to a certain extent.

Figure 13:
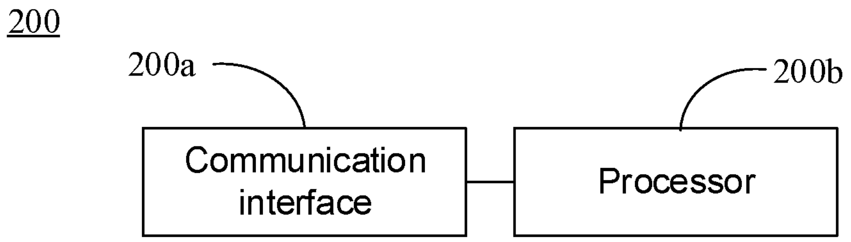
FIG. 13 is a structural diagram of a terminal, in accordance with some embodiments.

As shown in FIG. 13, some embodiments of the present disclosure provide a terminal 200. The terminal 200 includes a communication interface 200*a* and a processor 200*b*. The communication interface 200*a* is configured to receive a detection signal. The processor 200*b* is coupled to the communication interface 200*a*, and is configured to execute the remote operation control method as described in any of the above embodiments.

The detection signal may be any signal received by the terminal 200, and the embodiments of the present disclosure do not limit the content of the detection signal. For example, the detection signal may be a signal, transmitted by the first sensor 202, that includes the movement amount of the driving component 201 corresponding to the first sensor 202 detected by the first sensor 202. For another example, the detection signal may be a signal, transmitted by the second sensor 40, that includes the second position data and/or the second attitude data of the target device 30 detected by the second sensor 40. For yet another example, the detection signal may be the first operation signal of the operator (i.e., the user) instructing the control device 10 to control the simulation device 20 to move. For yet another example, the detection signal may be the second operation signal of the operator instructing the simulation device 20 to move to the set state.

Some embodiments of the present disclosure further provide a computer-readable storage medium (e.g., a non-transitory computer-readable storage medium). The computer-readable storage medium has stored computer program instruction(s) that, when run on a computer, cause the computer to execute the remote operation control method as described in any of the above embodiments.

For example, the non-transitory computer-readable storage medium may include, but is not limited to a magnetic storage device (e.g., a hard disk, a floppy disk or a magnetic tape), an optical disk (e.g., a compact disk (CD), a digital versatile disk (DVD)), a smart card and a flash memory device (e.g., an erasable programmable read-only memory (EPROM), a card, a stick or a key driver). Various computer-readable storage media described in the present disclosure may represent one or more devices and/or other machine-readable storage media for storing information. The term "machine-readable storage medium" may include, but is not limited to, wireless channels and various other media capable of storing, containing and/or carrying instructions and/or data.

Some embodiments of the present disclosure provide a computer program product. The computer program product includes computer program instructions that, when executed on a computer, cause the computer to perform one or more steps in the remote operation control method as described in the above embodiments.

Some embodiments of the present disclosure further provide a computer program. When executed on a computer, the computer program causes the computer to perform one or more steps in the remote operation control method as described in the above embodiments.

Beneficial effects that may be achieved by the terminal, the computer-readable to storage medium, the computer program product, and the computer program provided in some embodiments of the present disclosure are the same as the beneficial effects of the remote operation control method as described in the above embodiments of the present disclosure, and details will not be repeated herein.

The flowcharts and block diagrams in the drawings illustrate the possible implementations of the architecture, functions, and operations of the systems, methods, and computer program products provided in the embodiments of the present disclosure. In this regard, each block in the flow diagrams or block diagrams may represent a module, program segment, or portion of code, which contains one or more executable instructions for implementing the specified logic function(s). It will also be noted that, in some alternative implementations, the functions in the blocks may also occur in an order different from the order shown in the drawings. For example, two blocks shown in succession may actually be executed approximately in parallel, and they may sometimes be executed in the reverse order, depending on the functions involved. It will also be noted that, each block of the block diagrams and/or flowcharts, and combinations of blocks in the block diagrams and/or flowcharts may be implemented by a special purpose hardware-based system that performs the specified functions or operations, or by a combination of special purpose hardware and computer instructions.

The units described in the present disclosure may be implemented in software, or may be implemented in hardware. The name of the unit does not constitute a limitation on the unit itself under certain circumstances.

The functions described hereinabove may be performed at least in part by one or more hardware logic components. For example, without limitation, exemplary types of hardware logic components that may be used include: a field programmable gate array (FPGA), an application specific integrated circuit (ASIC), an application specific standard product (ASSP), a system on chip (SOC), a complex programmable logical device (CPLD), etc.

The above description is only some embodiments of the present disclosure and an explanation of the applied technical principles. A person of ordinary skill in the art will understand that the scope of disclosure involved in the present disclosure is not limited to technical solutions formed by a specific combination of the above technical features, and should also include other technical solutions formed by arbitrarily combining the above technical features and/or equivalent features thereof without departing from the above disclosed concept. For example, technical solutions formed by replacing the above technical features with technical features disclosed in the present disclosure that have similar functions (but it is not limited thereto).

In addition, although the operations are depicted in a specific order, this will not be understood as it is required that these operations be performed in a specific order shown herein or in a sequential order. Under certain circumstances, multitasking and parallel processing may be advantageous. Likewise, although several detailed implementations are included in the above description, these will not be construed as limiting the scope of the present disclosure. Certain features that are described in the context of separate embodiments may be implemented in combination in a single embodiment. Various features described in the context of a single embodiment may also be implemented in a plurality of embodiments individually or in any suitable sub-combination.

Although the subject matter has been described in language specific to structural features and/or logical actions of methods, it will be understood that the subject matter defined in the appended claims is not necessarily limited to the specific features or actions described above. The specific features and actions described above are merely exemplary forms of implementing the claims.

The foregoing descriptions are merely specific implementations of the present disclosure, but the protection scope of the present disclosure is not limited thereto. Any person skilled in the art could conceive of changes or replacements within the technical scope of the present disclosure, which shall be included in the protection scope of the present disclosure. Therefore, the protection scope of the present disclosure shall be subject to the protection scope of the claims.

What is claimed is:

1. A remote operation control system, comprising:

a simulation device;

a target device; and a control device coupled to the simulation device and the target device, the control device being configured to determine first position data and first attitude data of the simulation device when the simulation device moves to a set state, and control the target device to move to a same state as the set state based on the first position data and the first attitude data; and the control device being further configured to control the simulation device to move to the set state in response to a first operation of an operator instructing the simulation device to move; and determine whether the simulation device has moved to the set state in response to a second operation of the operator instructing the simulation device to move to the set state;

wherein the target device is a C-arm, and the simulation device is a simulated C-arm; the simulated C-arm includes an L-shaped part, a C-shaped part, and an X-axis rotary motion mechanism; the L-shaped part includes an X-axis linear motion mechanism, a Y-axis linear motion mechanism, and a Y-axis rotary motion mechanism connecting the X-axis linear motion mechanism and the Y-axis linear motion mechanism; the X-axis rotary motion mechanism connects the X-axis linear motion mechanism and the C-shaped part;

the Y-axis rotary motion mechanism is configured to make the X-axis linear motion mechanism rotate around a Y axis relative to the Y-axis linear motion mechanism; and the X-axis rotary motion mechanism is configured to make the C-shaped part rotate around an X axis relative to the X-axis linear motion mechanism.

2. The remote operation control system according to claim 1, wherein the simulation device includes:

at least one driving component coupled to the control device, the at least one driving component being configured to drive the simulation device to move to the set state under control of the control device; and at least one first sensor connected to the at least one driving component in one-to-one correspondence, each first sensor being configured to obtain a movement amount of a corresponding driving component connected to the first sensor when the simulation device moves from a previous state to the set state, wherein the control device is coupled to the at least one first sensor, and the control device is configured to determine the first position data and the first attitude data based on position data and attitude data of the simulation device when the simulation device is in the previous state, and a movement amount of the at least one driving component.

3. The remote operation control system according to claim 1, wherein the control device is further configured to:

obtain a current state of the target device;

generate a control instruction including a movement control amount based on second position data and second attitude data of the target device in the current state, and the first position data and the first attitude data; and send the control instruction to the target device, wherein the control instruction is used for controlling the target device to move to the same state as the set state.

4. The remote operation control system according to claim 3, wherein the movement control amount includes at least one linear displacement control amount and/or at least one rotation angle control amount.

5. The remote operation control system according to claim 3, further comprising:

at least one second sensor configured to detect the second position data and/or the second attitude data of the target device in the current state, wherein the control device is coupled to the at least one second sensor, and the control device is further configured to obtain the second position data and/or the second attitude data detected by the at least one second sensor.

6. The remote operation control system according to claim 3, further comprising:

an interaction device configured to obtain information of the current state of the target device, and display the information of the current state of the target device, wherein the information of the current state of the target device includes the second position data and the second attitude data of the target device, and/or an image of the target device.

7. The remote operation control system according to claim 6, wherein the interaction device is coupled to the control device, and the interaction device is configured to obtain the second position data and the second attitude data of the target device in the current state from the control device, and display the second position data and the second attitude data of the target device; and/or, the remote operation control system further comprises a photographing device coupled to the interaction device, the photographing device being configured to photograph the image of the target device, and send the image of the target device to the interaction device, so that the interaction device displays the image of the target device.

8. The remote operation control system according to claim 1, wherein the control device is further configured to: obtain a current state of the target device; and control the simulation device to move to the same state as the target device based on second position data and second attitude data of the target device in the current state, under a predetermined condition; or obtain a current state of the target device, and control the simulation device to move to the same state as the target device based on second position data and second attitude data of the target device in the current state, under a predetermined condition, wherein the predetermined condition includes at least one of fine-tuning a pose of the target device or resetting the target device to an initial state.

9. The remote operation control system according to claim 1, wherein the Y-axis linear motion mechanism includes:

a first motor configured to drive the X-axis linear motion mechanism to move linearly based on a first movement control amount; and a first encoder configured to detect a rotation amount of an output shaft of the first motor, so as to determine a linear movement amount of the X-axis linear motion mechanism;

the X-axis linear motion mechanism includes:

a second motor configured to drive the C-shaped part to move linearly based on a second movement control amount; and a second encoder configured to detect a rotation amount of an output shaft of the second motor, so as to determine a linear movement amount of the C-shaped part;

the Y-axis rotary motion mechanism includes:

a third motor configured to drive the X-axis linear motion mechanism to rotate relative to the Y-axis linear motion mechanism based on a third movement control amount; and a third encoder configured to detect a rotation amount of an output shaft of the third motor, so as to determine a rotation amount of the X-axis linear motion mechanism;

the X-axis rotary motion mechanism includes:

a fourth motor configured to drive the C-shaped part to rotate relative to the X-axis linear motion mechanism based on a fourth movement control amount; and a fourth encoder configured to detect a rotation amount of an output shaft of the fourth motor, so as to determine a rotation amount of the C-shaped part;

the C-shaped part includes:

a fixed structure, wherein a guide rail is provided on the fixed structure;

an arc-shaped structure slidably connected to the guide rail;

a fifth motor configured to drive the arc-shaped structure to rotate relative to the fixed structure based on a fifth movement control amount; and a fifth encoder configured to detect a rotation amount of an output shaft of the fifth motor, so as to determine a rotation amount of the arc-shaped structure.

10. A remote operation control method, comprising:

determining first position data and first attitude data of a simulation device when the simulation device moves to a set state; and controlling a target device to move to a same state as the set state based on the first position data and the first attitude data; and the remote operation control method further comprising:

controlling the simulation device to move to the set state in response to a first operation of an operator instructing the simulation device to move; and determining whether the simulation device has moved to the set state in response to a second operation of the operator instructing the simulation device to move to the set state;

wherein the target device is a C-arm, and the simulation device is a simulated C-arm; the simulated C-arm includes an L-shaped part, a C-shaped part, and an X-axis rotary motion mechanism; the L-shaped part includes an X-axis linear motion mechanism, a Y-axis linear motion mechanism, and a Y-axis rotary motion mechanism connecting the X-axis linear motion mechanism and the Y-axis linear motion mechanism; the X-axis rotary motion mechanism connects the X-axis linear motion mechanism and the C-shaped part;

the Y-axis rotary motion mechanism is configured to make the X-axis linear motion mechanism rotate around a Y axis relative to the Y-axis linear motion mechanism; and the X-axis rotary motion mechanism is configured to make the C-shaped part rotate around an X axis relative to the X-axis linear motion mechanism.

11. The remote operation control method according to claim 10, wherein determining the first position data and the first attitude data of the simulation device when the simulation device moves to the set state includes:

obtaining a movement amount of at least one driving component in the simulation device when the simulation device moves from a previous state to the set state; and determining the first position data and the first attitude data based on position data and attitude data of the simulation device when the simulation device is in the previous state, and the movement amount of the at least one driving component.

12. The remote operation control method according to claim 10, wherein controlling the target device to move to the same state as the set state based on the first position data and the first attitude data includes:

obtaining a current state of the target device;

generating a control instruction including a movement control amount based on second position data and second attitude data of the target device in the current state, and the first position data and the first attitude data; and sending the control instruction to the target device, wherein the control instruction is used for controlling the target device to move to the same state as the set state.

13. The remote operation control method according to claim 12, wherein the movement control amount includes at least one linear displacement control amount and/or at least one rotation angle control amount.

14. The remote operation control method according to claim 10, further comprising:

obtaining a current state of the target device, and controlling the simulation device to move to the same state as the target device based on second position data and second attitude data of the target device in the current state, under a predetermined condition.

15. The remote operation control method according to claim 14, wherein the predetermined condition includes at least one of following:

fine-tuning a pose of the target device; or resetting the target device to an initial state.

16. A non-transitory computer-readable storage medium having stored at least one computer program instruction that, when run on a computer, cause the computer to execute the remote operation control method according to claim 10.

* * * * *